United States Patent
Wang

(10) Patent No.: US 10,624,881 B2
(45) Date of Patent: Apr. 21, 2020

(54) METHODS FOR INDUCING APOPTOSIS IN CANCER CELLS

(71) Applicant: Health Research, Inc., Buffalo, NY (US)

(72) Inventor: Xinjiang Wang, Buffalo, NY (US)

(73) Assignee: Health Research, Inc., Buffalo, NY (US)

(*) Notice: Subject to any disclaimer, the term of this patent is extended or adjusted under 35 U.S.C. 154(b) by 0 days.

(21) Appl. No.: 15/767,599

(22) PCT Filed: Oct. 12, 2016

(86) PCT No.: PCT/US2016/056534
§ 371 (c)(1),
(2) Date: Apr. 11, 2018

(87) PCT Pub. No.: WO2017/066245
PCT Pub. Date: Apr. 20, 2017

(65) Prior Publication Data
US 2018/0289693 A1    Oct. 11, 2018

Related U.S. Application Data

(60) Provisional application No. 62/240,097, filed on Oct. 12, 2015.

(51) Int. Cl.
*A61K 31/4709*   (2006.01)
*A61K 31/496*    (2006.01)
*A61P 35/00*     (2006.01)

(52) U.S. Cl.
CPC ........ *A61K 31/4709* (2013.01); *A61K 31/496* (2013.01); *A61P 35/00* (2018.01); *A61K 2300/00* (2013.01)

(58) Field of Classification Search
CPC .......................... C07D 401/12; A61K 31/4709
See application file for complete search history.

(56) References Cited

U.S. PATENT DOCUMENTS

| 2010/0150844 A1 | 6/2010 | Zhang et al. |
| 2012/0156197 A1* | 6/2012 | Errico .................. C07K 16/44 424/133.1 |
| 2013/0131096 A1* | 5/2013 | Puskas ................ C07D 215/26 514/275 |
| 2014/0212414 A1 | 7/2014 | Oh et al. |
| 2015/0105412 A1 | 4/2015 | Errico et al. |

FOREIGN PATENT DOCUMENTS

| WO | 2012/047587 A2 | 4/2012 |
| WO | WO2012/047587 | * 12/2012 |
| WO | 2014/028886 A1 | 2/2014 |

OTHER PUBLICATIONS

Schormann et al., Identification of Protein-Protein Interaction Inhibitors Targeting Vaccinia Virus Processivity Factor or Development of Antiviral Agents, Antimicrobial Agents and Chemotherapy, Nov. 1, 2011, pp. 5054-5062, vol. 55, No. 11.

Lu et al., Discovery of a Nanomolar Inhibitor of the Human Murine Double Minute 2 (MDM2)-p53 Interaction Through an Integrated, Virtual Database Screening Strategy, Journal of Medicinal Chemistry, May 26, 2006, pp. 3759-3762, vol. 49, No. 13.

* cited by examiner

*Primary Examiner* — Rei Tsang Shiao
(74) *Attorney, Agent, or Firm* — Hodgson Russ LLP

(57) ABSTRACT

Provided are methods for inducing apoptosis of cells using quinolinol compounds. Combinations of quinolinol compounds can be used in the methods. Combinations of one or more quinolinol compound and one or more inhibitors of cell growth arrest, e.g., Nutlin3a, can also be used in the methods. Also provided are compositions comprising of one or more quinolinol compound and one or more pharmaceutically acceptable carrier. The compositions can comprise one or more quinolinol compound, one or more pharmaceutically acceptable carrier, and one or more inhibitors of cell growth arrest, e.g., Nutlin3a.

5 Claims, 10 Drawing Sheets

METHODS FOR INDUCING APOPTOSIS IN CANCER CELLS

CROSS REFERENCE TO RELATED APPLICATIONS

This application claims priority to U.S. Provisional Application No. 62/240,097, filed on Oct. 12, 2015, the disclosure of which is hereby incorporated by reference.

FIELD OF THE DISCLOSURE

The disclosure generally relates to quinolinol compounds for cancer therapy and methods of using same. More particularly the disclosure relates to quinolinol compounds for activation of p53 and methods of using same.

BACKGROUND OF THE DISCLOSURE

Activation of tumor suppressor p53 as a targeted nongenotoxic cancer therapy has been pursued enthusiastically for many years, because p53 possesses potent tumor suppressing activity in vivo. p53 can terminate cancer cell growth by induction of apoptosis and senescence and inhibit cancer cell growth by cell cycle arrest. The p53-based therapy is particularly attractive for cancer types including retinoblastoma, neuroblastoma and leukemia/lymphoma in which p53 is rarely mutated and p53-dependent apoptosis pathway is a predominant endpoint in these cancer cells. Except for cancer-selected p53 mutations, the tumor suppressor activity of p53 is mainly inhibited by p53-binding proteins Mdm2 and MdmX in normal and cancer cells. Prior focus of p53 reactivation strategy has been on targeting the Mdm2-p53 interface, and/or MdmX-p53 interface. Exploration of these inhibitors led to discovery of a list of potent Mdm2 inhibitors, several compounds of this class have been advanced to Phase I clinical trials in hematological neoplasia and solid tumors. However, the therapeutic effects of Mdm2 inhibitors can be attenuated by MdmX overexpression. Although peptide inhibitors of dual function for inhibiting both Mdm2-p53 and MdmX-p53 interaction will overcome this problem and enhance p53-dependent cancer killing, these inhibitors will not inhibit Mdm2 E3 ligase activity toward non-p53 targets such as RB, p21 and DAXX, which to different extent affects the p53-dependent biological effects.

The TP53 pathway is the most frequently inactivated pathway in human cancer. Overexpression of Mdm2 and MdmX (aka Mdm4) is the major mechanism for inactivation of p53 protein function in hematological malignancies. Targeting Mdm2-p53 interface has been a focus for development of anti-cancer drugs for p53 restoration in cancer therapy. However, MdmX overexpression confers resistance to this type of inhibitors such as Nutlin3a.

Recent genetic studies indicated that RING domains of Mdm2 and MdmX are required for in vivo inhibition of p53 activity during development. MdmX was reported to stimulate Mdm2-mediated p53 multiple monoubiquitination using GST-fusion Hdm2 proteins.

SUMMARY OF THE DISCLOSURE

The present disclosure provides compositions and methods for inhibiting the growth of cells and/or causing apoptosis. For example, the compositions and methods cause apoptosis of cancer cells. The compositions comprise one or more inhibitors of Mdm2-Mdmx RING-RING interaction. The compositions may also comprise one or more inhibitors of other pathways for cell growth arrest, such as, for example, inhibitors of gene p21. For example, the composition can comprise one or more inhibitors of Mdm2-Mdmx RING-RING interaction and one or more inhibitors of direct interaction of MdmX or Mdm2 with p53. An example of an agent that inhibits interaction of Mdmx or Mdm2 with p53 is Nutlin3a.

In an aspect, the present disclosure provides quinolinol compounds. The quinolinol compounds can inhibit Mdm2-Mdmx RING-RING interaction. In an example, the quinolinol compound is selected from MMRi61, MMRi62, MMRi64, MMRi68, and combinations thereof.

In an aspect, the present disclosure provides compositions comprising one or more quinolinol compound (e.g., MMRi6 and/or its analogs (referred to herein as the MMRi6 family of compounds)) in a pharmaceutically acceptable carrier. The compositions may be formulated to provide a therapeutically effective dose of the quinolinol compound(s) (e.g., MMRi6 family of compounds). For example, a composition further comprises an inducer of apoptosis and an inhibitor of cell growth-arrest (e.g., Nutlin3a).

In an aspect, the present disclosure provides methods for causing apoptosis of cells by contacting the cells with a composition comprising one or more quinolinol compound (e.g., one or more members of the MMRi6 family of compounds), and optionally further comprising one or more inhibitors of cell growth arrest. For example, the cells may be contacted with MMRi6, MMRi61, MMRi62, MMRi63, MMRi64, MMRi65, or a combination thereof, and may also be contacted with Nutlin3a. The cells may be contacted in vitro or in vivo. The cells may be contacted with a quinolinol compound (e.g., MMRi6 family) and Nutlin3a simultaneously or sequentially. A measure of effectiveness of the quinolinol compound(s) (e.g., MMRi6, MMRi61, MMRi62, MMRi63, MMRi64, MMRi65, or a combination thereof) is determination of Mdm2-Mdmx E3 ligase activity. The methods can induce apoptosis in cancer cells (e.g., leukemia and lymphoma cells). The quinolinol compound(s) or composition comprising the quinolinol compound(s) can be administered to an individual (e.g., a human or non-human animal) such as, for example, an individual that has cancer (e.g., leukemia or lymphoma).

BRIEF DESCRIPTION OF THE FIGURES

For a fuller understanding of the nature and objects of the disclosure, reference should be made to the following detailed description taken in conjunction with the accompanying figures.

Figure 2:
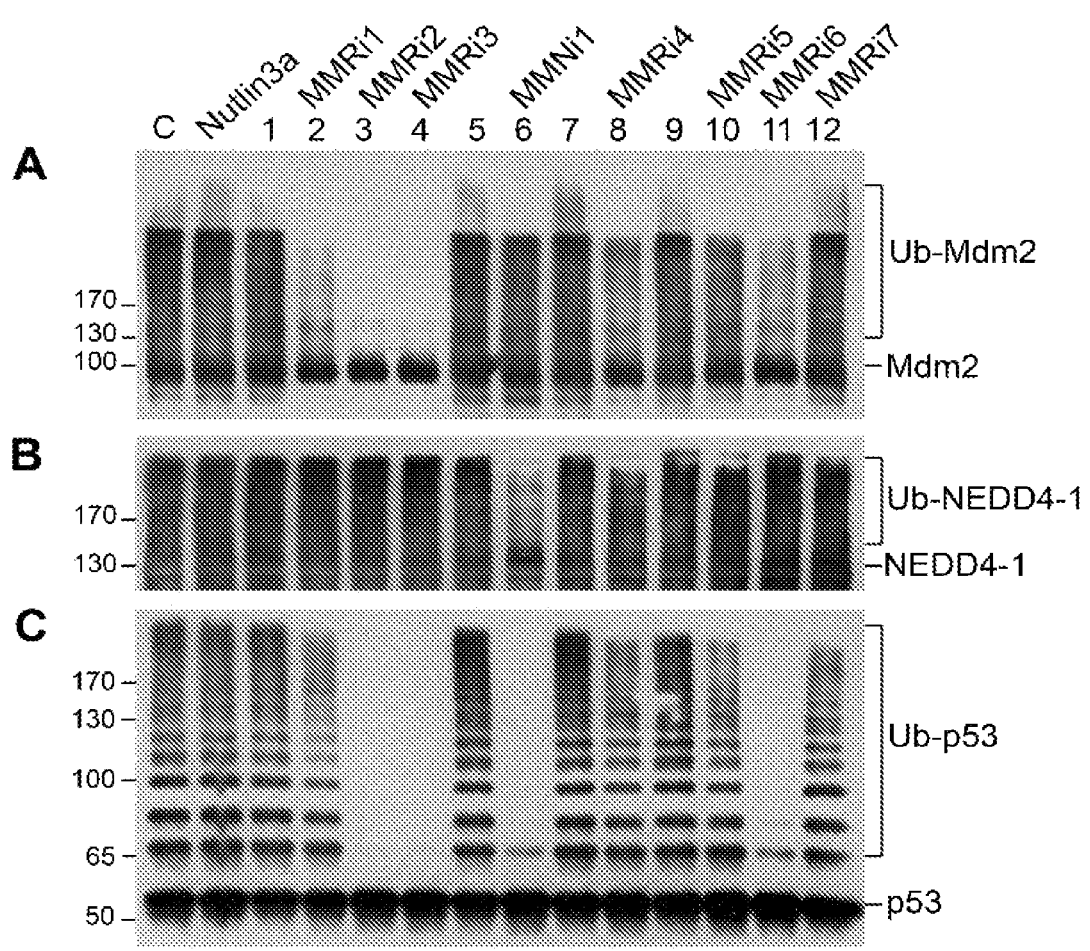

FIG. 2 shows in vitro validation of HTS hits by ubiquitination assays. (A) Effects of hits on Mdm2 ubiquitination by Mdm2-MdmX complex. Mdm2 (100 nM) and MdmX (200 nM) were used in the in vitro ubiquitination reaction in the presence of hits (10 µM) or Nutlin3a (10 µM) or DMSO (10 µM) as a control (C), followed by WB of Mdm2 with anti-HA antibody. Ubiquitinated Mdm2 is shown as Ub-Mdm2. (B) Effects of hits on NEDD4-1 autoubiquitination. In vitro ubiquitination reaction was carried out with NEDD4-1 (200 nM) as described in (A) followed by WB for NEDD4-1 with a rabbit antibody. Ubiquitinated NEDD4-1 is shown as Ub-NEDD4-1. (C) Effects of hits on p53 ubiquitination by Mdm2-MdmX. In vitro ubiquitination reaction was carried out as described in A expect for addition of 200 nM of p53 recombinant proteins, followed by WB of p53 with DO-1 and PAb1801 mixture.

Figure 3:
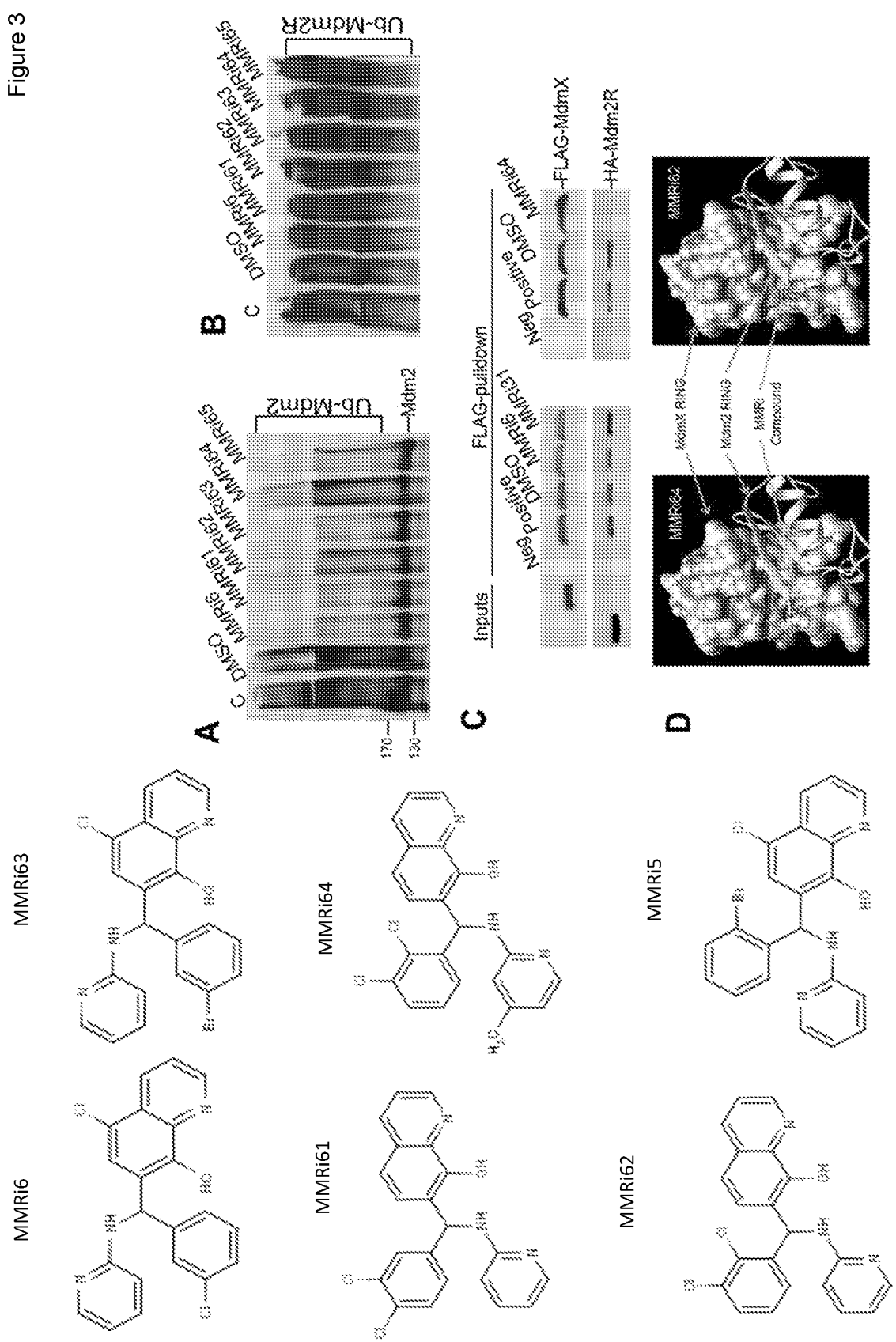

FIG. 3 shows inhibition of Mdm2-MdmX RING-RING interaction by MMRi6 and its analogue MMRi64. (A) Effect of MMRi6 and its analogues on the E3 ligase activity of Mdm2-MdmX with Mdm2 autoubiquitination as a readout. In vitro ubiquitination assays were performed with Mdm2 (100 nM) and MdmX (200 nM) in the presence of nothing (C), DMSO (10 µM) or indicated compounds (10 µM), followed by WB of Mdm2 with anti-HA antibody. (B) Effect of MMRi6 and its analogues on the E3 ligase activity of Mdm2-RING domain. In vitro ubiquitination assays were performed with Mdm2-RING domain (100 nM) in the presence of nothing (C), DMSO (10 µM) or indicated compounds (10 µM), followed by WB of Mdm2 with anti-HA. (C) Effect of MMRis on interaction of Mdm2 and MdmX proteins in vitro. FLAG-MdmX and HA-Mdm2-RING domain (HA-Mdm2R) were incubated in vitro in the presence of nothing (positive control), or DMSO (10 µM) or indicated compounds (10 µM), followed by pulldown with anti-FLAG-beads (M2) and WB of MdmX and Mdm2-RING domain with anti-FLAG and anti-HA antibodies respectively. The negative control (Neg) contains all components as in positive control sample except for missing of FLAG-MdmX. (D) Chemical structures of MMRi6, MMRi61, MMRi62, MMRi63, MMRi64, and MMRi65. (E) Docking analysis of MMRi64 and MMRi62 with 3-D structures of Mdm2-MdmX RING domains. The MMRi62 and MMRi64 (pink) bind to MdmX RING domain (Connolly surface) and interfere with its interaction with Mdm2 RING domain (ribbon diagram).

Figure 4:
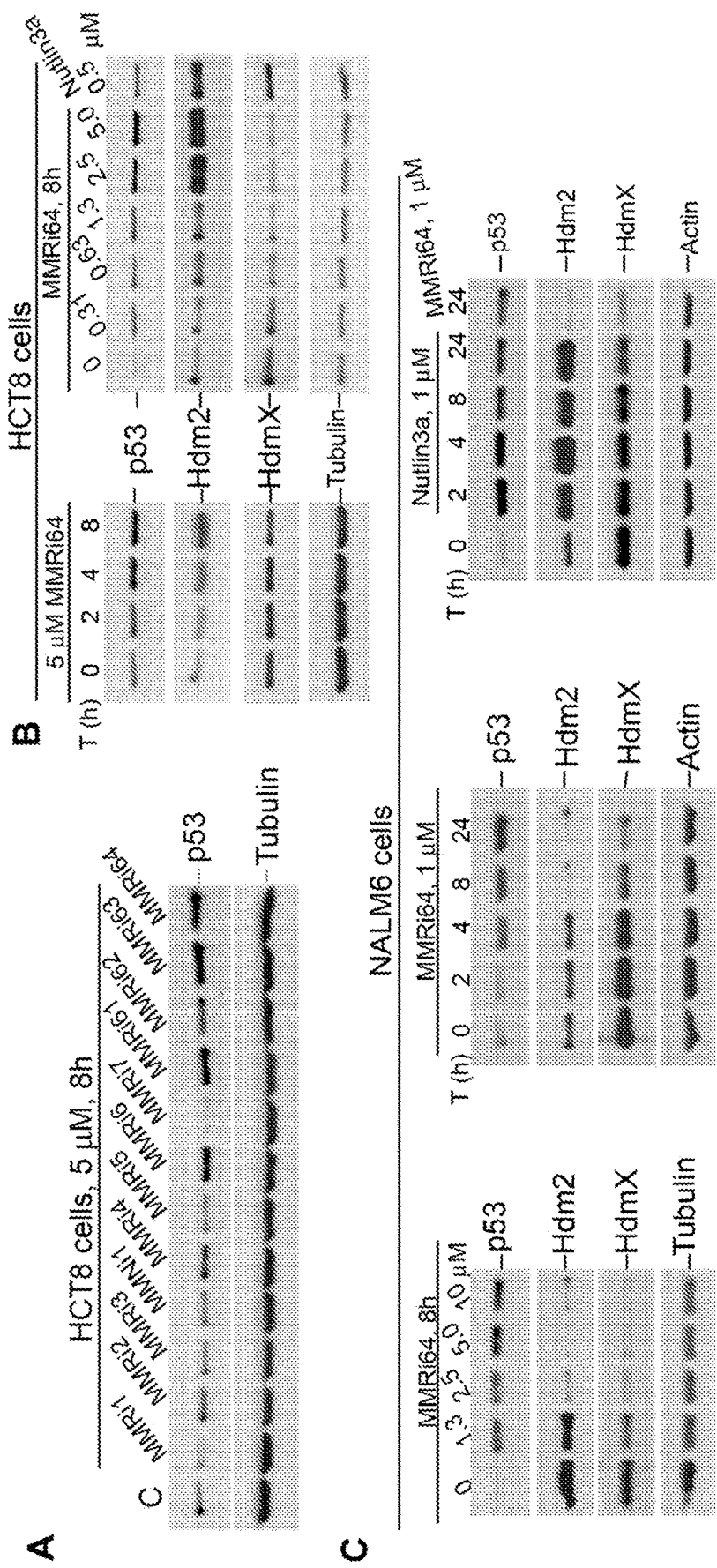

FIG. 4 shows that MMRis activate the p53 pathway in cancer cell lines. (A) p53 protein accumulation in MMRi-treated HCT8 cells. HCT8 cells were treated with indicated compounds (5 µM) for 8 hours and the whole cell lysates were analyzed by WB of p53 with tubulin as a loading control. (B) Time and concentration-dependent induction of p53 and Mdm2 accumulation by MMRi64 in HCT8 cells. HCT8 cells were treated at the indicated concentrations of MMRi64 (right) for 8 h and for the indicated time at 5 µM (left) and whole cell lysates were analyzed by WB of HdmX, Hdm2 and p53 and Tubulin was used for loading control. (C) Activation of the p53 pathway by MMRi64 and Nutlin3a in NALM6 lymphoma cells. Whole cell lysates were prepared from time course treatment of NALM6 cells with 1 µM of Nutlin3a and followed by WB for p53, Hdm2, HdmX and actin. NALM6 cells were treated for indicated time at the indicated concentrations of MMRi64 and the whole cell lysates were analyzed by WB for p53, Hdm2, HdmX and Tubulin.

Figure 5:
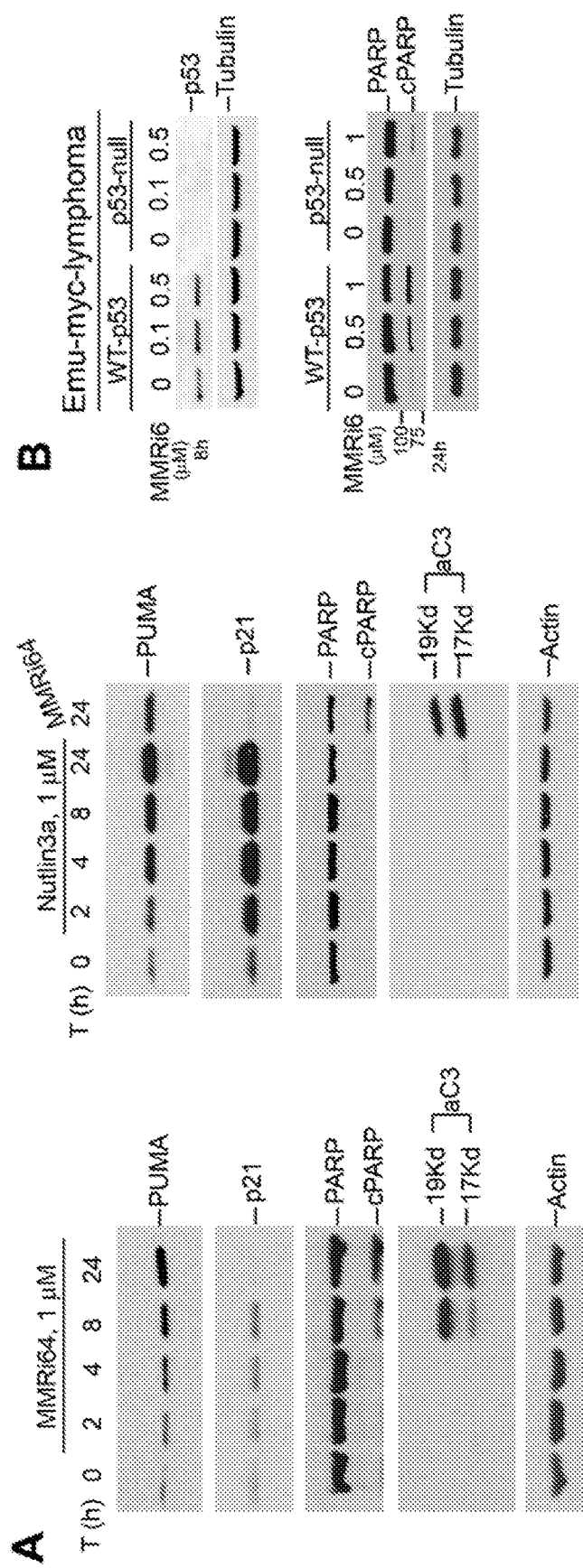
Figure 5:
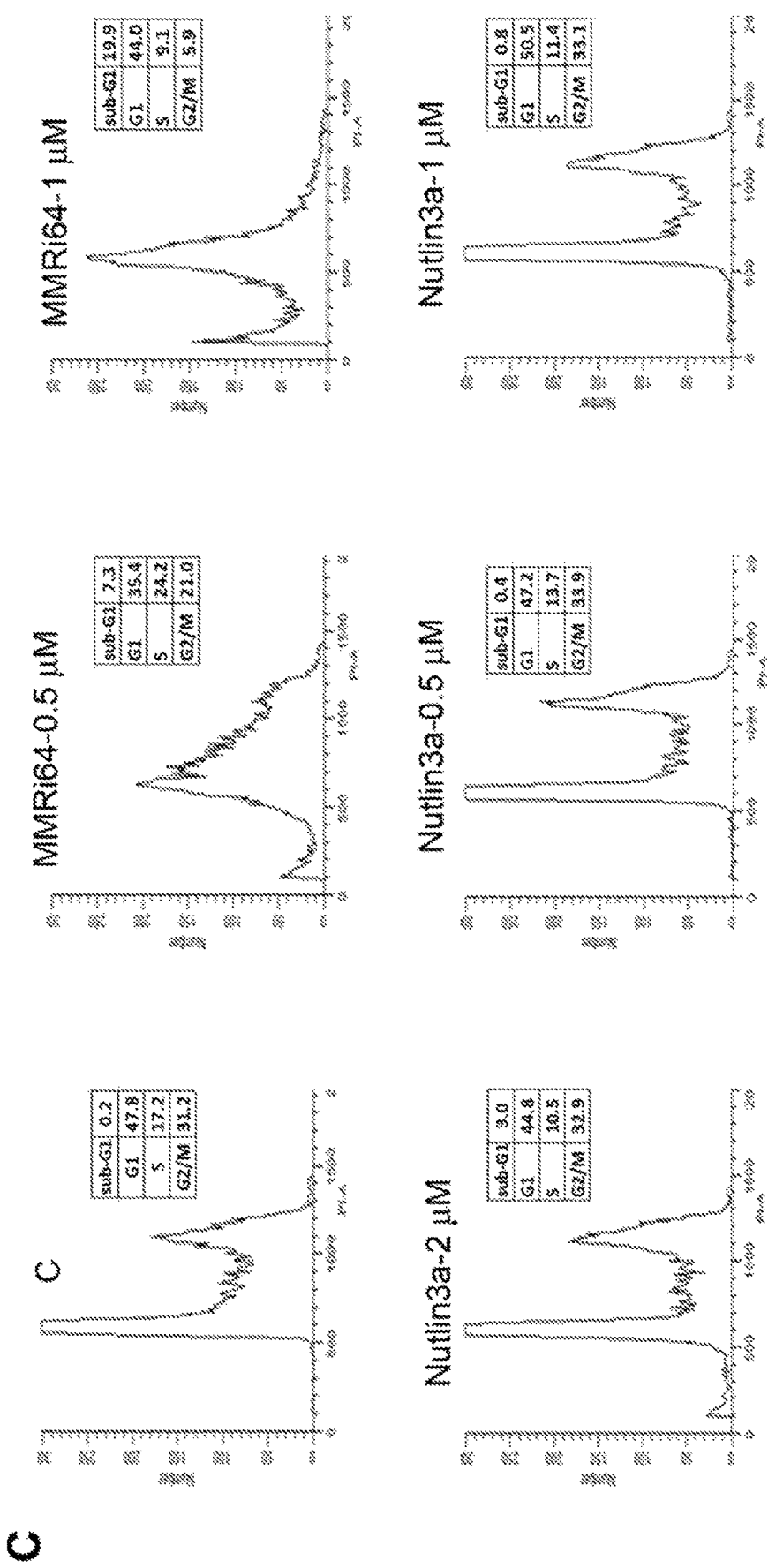

FIG. 5 shows that MMRi64 preferentially induces apoptosis in lymphoma cells. (A) MMRi64 is better inducer of apoptotic response than Nutlin3a in NALM6 cells. Whole cell lysates were prepared from time course treatment of NALM6 cells with 1 µM of MMRi64 (left) or Nutlin3a (right) and followed by WB for PUMA, p21, PARP, active caspase 3 (aC3) and actin. (B) Effects of p53 status on MMRi64-induced PARP cleavage in Emu-myc lymphoma cells. The Emu-myc lymphoma cells of different p53 status were treated with 0.1 µM and 0.5 µM of MMRi64 for 8 h and whole lysates were subjected to WB for p53 (upper panel); or the cells were treated with 0.5 µM and 1 µM of MMRi64 for 24 h for WB of PARP with Tubulin serving as loading control. (C) MMRi64 more effectively induces apoptosis analysis revealed by flow cytometry. Equimolar concentration of MMRi64 and Nutlin3a (1 µM) was used to treat NALM6 cells for 24 h followed by flow cytometry analysis after fixation and PI-staining of the cells. Sub-G1 fractions of each treatment were shown.

Figure 6:
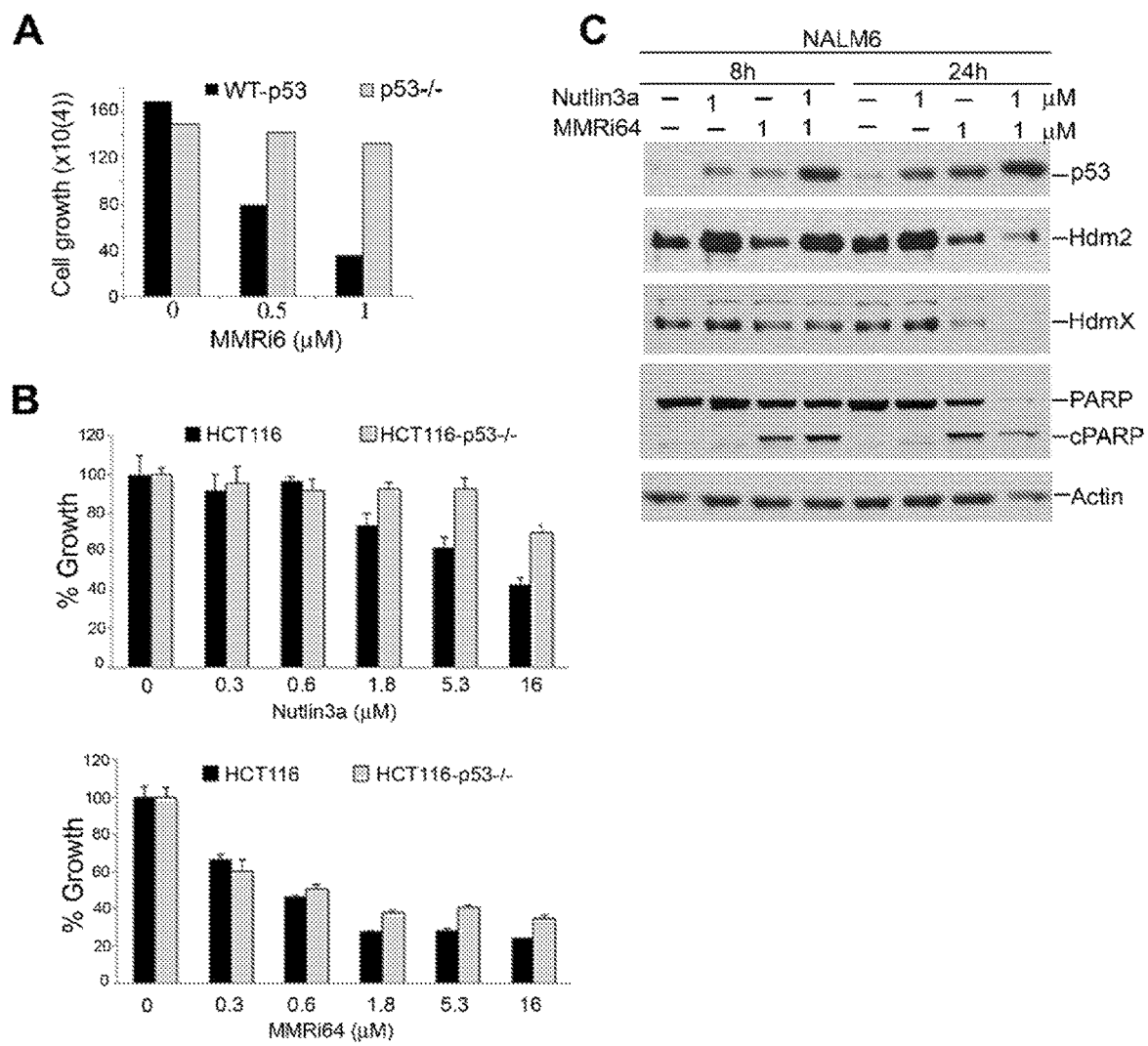
Figure 6:
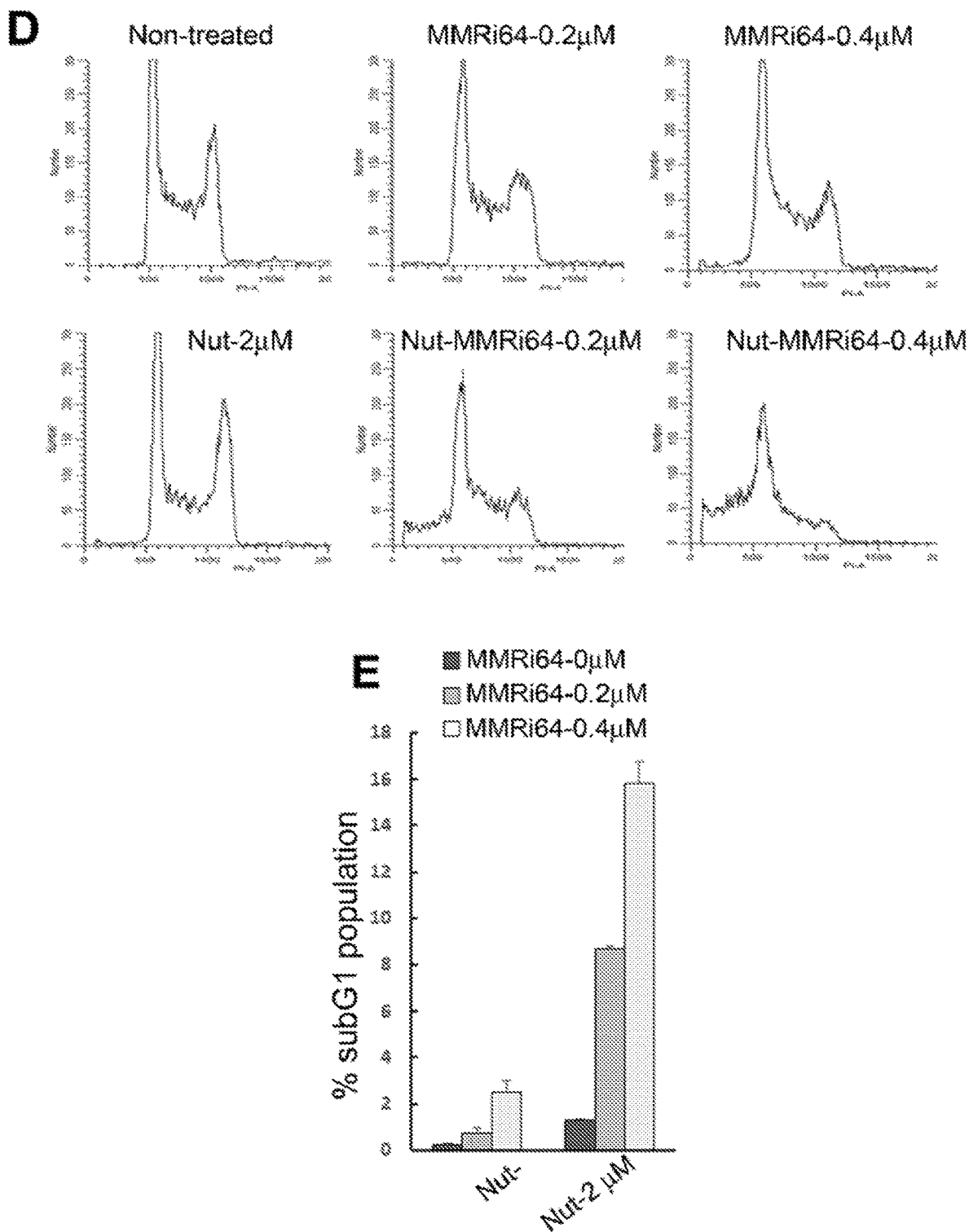

FIG. 6 shows MMRi64 lymphoma cell growth via p53-dependent and p53-indpendent mechanisms. (A) Effects of p53 status on MMRi64-induced growth inhibition in Emu-myc lymphoma cells. The ouse Emu-myc lymphoma cells of different p53 status were cultured in the presence of 0.5 µM and 1 µM of MMRi64 and the numbers of viable cells were counted by trypan blue exclusion at 72 h of treatment and plotted in histograms. (B) Effect of p53 status on Nutlin3a and MMRi64 sensitivity in colon cancer cells. HCT116 and HCT116-p53−/− cells were treated with indicated concentrations of drugs for 72 h and drug-induced growth inhibition was measured by MTT method and plotted in histograms. (C) Effect of MMRi64-Nutlin3a combination on expression of p53, Mdm2 and MdmX and apoptotic cleavage of PARP in NALM6 cells. WB analysis of p53, Mdm2 and MdmX and PARP cleavage after NALM6 cells were treated with Nutlin3a (1 µM) and MMRi64 (1 µM) alone or in combination for 8 h and 24 h. (D) Flow cytometric analysis of NALM6 cells treated with indicated concentrations of Nutlin3a and MMRi64 alone or in combination for 48 h. Cells were fixed and stained with PI and subjected to flow cytomteric analysis. (E) Histograms of Sub-G1 populations induced by MMRi64 or Nutlin3a alone or in their combinations at the indicated concentrations.

Figure 7:
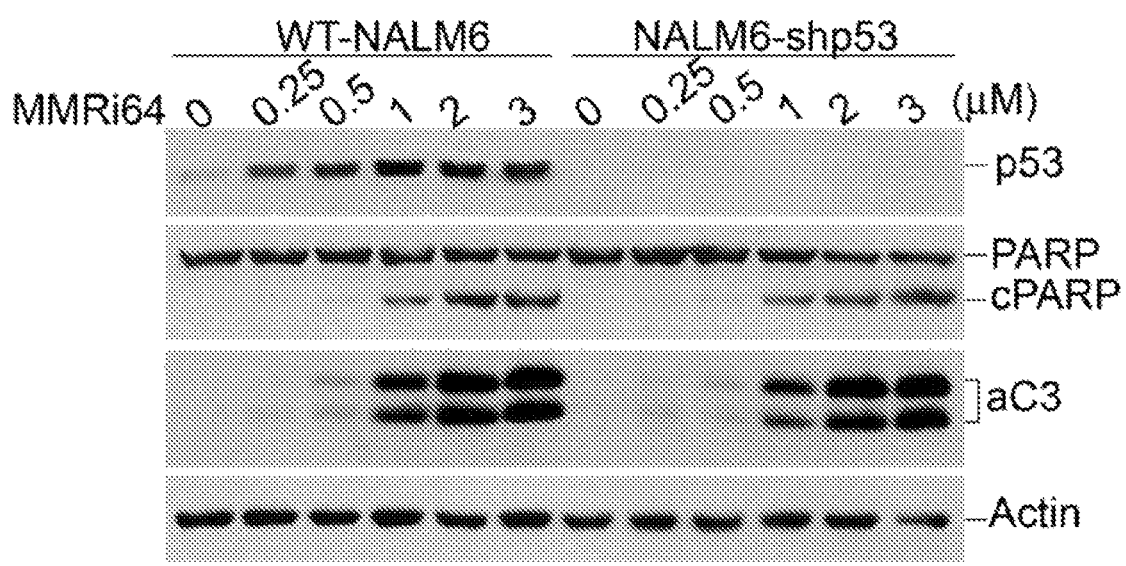

FIG. 7 shows p53 is not required for MMRi64-induced apoptosis. ShRNA knockdown of p53 in NALM6 cells did not affect apoptosis induction by MMRi64, nor did it affect MMRi64 selectivity in an anti-proliferation assay (Table 1). NALM6 cells or NALM6-shp53 cells were treated with MMRi64 at the indicated concentrations for 24 h, followed by western blotting analysis of p53 and caspase 3 activation (aC3) and apoptotic PARP cleavage (cPARP). Actin was the loading control.

DETAILED DESCRIPTION OF THE DISCLOSURE

In the this application, reference is made to the accompanying drawings that form a part hereof, and in which is shown by way of illustration specific examples and/or embodiments which may be practiced. These examples and/or embodiments are described in detail to enable those skilled in the art to practice the invention, and it is to be understood that other examples and/or embodiments may be utilized and that structural and logical changes may be made without departing from the scope of the present disclosure. The examples and/or embodiments provided herein are, therefore, not to be taken in a limited sense.

Although the present disclosure has been described for the purpose of illustration, it is understood that such detail is solely for that purpose and variations can be made by those skilled in the art without departing from the spirit and scope of the disclosure which is defined by the following claims.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

The present disclosure provides compositions and methods for inhibiting the growth of cells and/or causing apoptosis. For example, the compositions and methods cause apoptosis of cancer cells. The compositions comprise one or more inhibitors of Mdm2-Mdmx RING-RING interaction. The compositions may also comprise one or more inhibitors of other pathways for cell growth arrest, such as, for example, inhibitors of gene p21. For example, the composition can comprise one or more inhibitors of Mdm2-Mdmx RING-RING interaction and one or more inhibitors of direct interaction of MdmX or Mdm2 with p53. An example of an agent that inhibits interaction of Mdmx or Mdm2 with p53 is Nutlin3a.

The present disclosure describes identification and characterization of small molecule inhibitors for inactivation of Mdm2-MdmX RING-RING interaction in a high throughput screening effort. For example, MMRi64 disrupts Mdm2-MdmX interaction in vitro and activates the p53 pathway in cells and induces apoptosis in cells (e.g., cancer cells such as, for example, leukemia/lymphoma cells. This novel class of inhibitors can be useful in p53 studies and targeted cancer therapy.

The present disclosure provides reactivation of tumor suppressor p53 for targeted cancer therapy as an attractive strategy for cancers bearing, for example, wild type (WT) p53. Identification and characterization of small molecule inhibitors targeting Mdm2-MdmX RING-RING interaction as a new class of p53-reactivating agents is described. With a FRET-based E3 activity assay in a high-throughput screening (HTS) of a chemical library, we identified compounds (designated as MMRis) that specifically inhibit Mdm2-MdmX E3 ligase activity toward Mdm2 and p53 substrates but not the activity of NEDD4-1 E3 ligase. For example, MMRi6 and its analog MMRi64 are capable of disrupting Mdm2-MdmX interaction in vitro and activating p53 in cells. In leukemia cells, MMRi64 potently induces downregulation of Mdm2 and MdmX. In contrast to Nutlin3a, MMRi64 only induces expression of pro-apoptotic gene PUMA with little induction of growth-arresting gene p21. As a result, MMRi64 potently induces apoptosis in leukemia/lymphoma cells than Nutlin3a. Owing to distinct mechanisms of action of MMRi64 and Nutlin3a, their combination synergistically induces p53 and apoptosis. Taken together, Mdm2-MdmX plays a important role in apoptotic response of the p53 pathway and quinolinol compounds such as, for example, MMRi64 can be useful as both pharmacological tools for p53 studies and in, e.g., leukemia/lymphoma drug development.

The following are selected features of the present disclosure:

Small molecule inhibitors targeting Mdm2-MdmX RING domain interaction (MMRi) were identified by high throughput screening.

E.g., MMRi64 selectively induces PUMA, the pro-apoptotic target gene of p53 with little effect on growth-arresting gene p21.

E.g., MMRi64 strongly downregulates Mdm2 and MdmX in leukemia cells.

E.g., MMRi64 potently induces apoptosis while targeting Mdm2-p53 by Nutlin3a induces growth arrest in leukemia/lymphoma cells.

E.g., a combination of MMRi64 and Nutlin3 synergistically induces apoptosis.

In an aspect, the present disclosure provides quinolinol compounds. The quinolinol compounds can inhibit Mdm2-Mdmx RING-RING interaction.

Examples of suitable inhibitors of Mdm2-Mdmx RING-RING interaction are certain quinolinol compounds. The quinolinol compounds can be quinolinol derivatives. The quinolinol compounds can have one of the following structures:

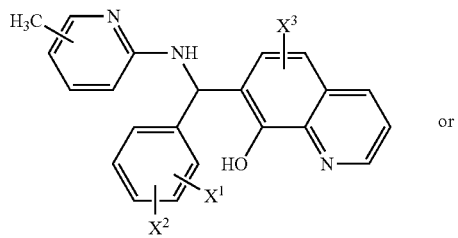

or

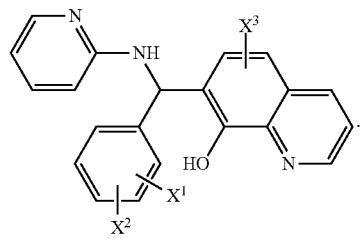

$X^1$, $X^2$, and $X^3$ substituents at any of position of the indicated ring and are independently selected from —H, —Cl, —Br, and —I. $CH_3$ is an optional substituent at any position on the pyridine ring. For example, quinolinol compounds MMRi6 and its analogs can be used in the present compositions and methods. Examples of MMRi6 analogs include MMRi61, MMRi62, MMRi63, MMRi64, and MMRi65. Thus, the compositions can comprise one or more quinolinol compound (e.g., MMRi6, MMRi61, MMRi62, MMRi63, MMRi64, MMRi65, or a combination thereof), and optionally further comprise Nutlin3a or other inhibitors of cell growth arrest.

Examples of quinolinol compounds include, but are not limited to, the following:

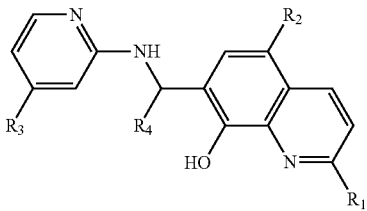
| Compounds | $R_1, R_2, R_3$ | $R_4$ | MV4-11 | NALM-6 | shP53-NALM-6 | CCRF-CEM |
|---|---|---|---|---|---|---|
| MMRi6 (207) | $R_1$ = H<br>$R_2$ = Cl<br>$R_3$ = H | 3-chlorophenyl | 0.51 | 0.46 | 0.66 | 1.07 |
| MMRi61 (207-1) | $R_1$ = H<br>$R_2$ = H<br>$R_3$ = H | 3,4-dichlorophenyl | 0.25 | 0.16 | 0.16 | 0.32 |
| MMRi62 (207-2) | $R_1$ = H<br>$R_2$ = H<br>$R_3$ = H | 2,3-dichlorophenyl | 0.22 | 0.11 | 0.12 | 0.19 |
| MMRi63 (207-3) | $R_1$ = H<br>$R_2$ = Cl<br>$R_3$ = H | 3-bromophenyl | 0.44 | 0.39 | 0.45 | 0.79 |
| MMRi64 (207-4) | $R_1$ = H<br>$R_2$ = H<br>$R_3$ = $CH_3$ | 2,3-dichlorophenyl | 0.26 | 0.15 | 0.14 | 0.24 |
| MMRi65 (207-5) | $R_1$ = H<br>$R_2$ = Cl<br>$R_3$ = H | 2-bromophenyl | 0.47 | 0.47 | 0.48 | 0.77 |

-continued
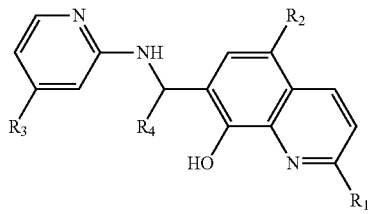
| Compounds | $R_1, R_2, R_3$ | $R_4$ | MV4-11 | NALM-6 | shP53-NALM-6 | CCRF-CEM |
|---|---|---|---|---|---|---|
| MMRi66 (207-6) | $R_1$ = H<br>$R_2$ = Cl<br>$R_3$ = H | 4-nitrophenyl | 0.32 | 0.40 | 0.47 | 0.61 |
| MMRi67 (207-7) | $R_1$ = H<br>$R_2$ = Cl<br>$R_3$ = H | 4-carboxybenzene | 4.46 | 3.75 | 6.10 | 9.79 |
| MMRi68 (207-8) | $R_1$ = H<br>$R_2$ = H<br>$R_3$ = $CH_3$ | 2,6-dichlorophenyl | 0.30 | 0.19 | 0.21 | 0.37 |
| MMRi69 (207-9) | $R_1$ = H<br>$R_2$ = H<br>$R_3$ = $CH_3$ | 2,4-dichlorophenyl | 0.28 | 0.28 | 0.24 | 0.48 |
| MMRi610 (207-10) | $R_1$ = H<br>$R_2$ = Cl<br>$R_3$ = H | 2-chloro-6-fluorophenyl | 0.72 | 0.42 | 0.49 | 0.73 |

-continued

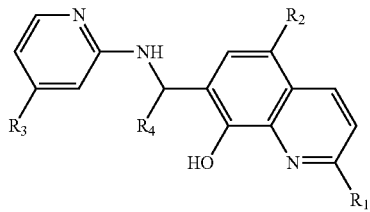

| Compounds | $R_1, R_2, R_3$ | $R_4$ | MV4-11 | NALM-6 | shP53-NALM-6 | CCRF-CEM |
|---|---|---|---|---|---|---|
| MMRi611 (207-11) | $R_1$ = H<br>$R_2$ = Cl<br>$R_3$ = H | 5-bromo-2-methoxyphenyl | 0.44 | 0.27 | 0.30 | 0.61 |
| MMRi612 (207-12) | $R_1$ = CH$_3$<br>$R_2$ = H<br>$R_3$ = H | 4-hydroxyphenyl | 5.75 | 2.48 | 3.98 | 4.43 |
| MMRi613 (207-13) | $R_1$ = H<br>$R_2$ = Cl<br>$R_3$ = H | 3-nitrophenyl | 0.47 | 0.38 | 0.43 | 0.80 |

In an example, the quinolinol compound is selected from MMRi61, MMRi62, MMRi64, MMRi68, and combinations thereof.

In an aspect, the present disclosure provides compositions comprising one or more quinolinol compound (e.g., MMRi6 and/or its analogs (referred to herein as the MMRi6 family of compounds)) in a pharmaceutically acceptable carrier. The compositions may be formulated to provide a therapeutically effective dose of the quinolinol compound(s) (e.g., MMRi6 family of compounds). A therapeutically effective dose is a dose that can result in amelioration of symptoms associated with the indication the composition is intended to treat (e.g., a cancer such leukemia or lymphoma). A therapeutically effective dose may be a single administration or may be multiple administrations that make up a treatment regimen.

For example, a composition comprises an inducer of apoptosis and an inhibitor of cell growth-arrest. In another example, a composition comprises one or more quinolinol compound (e.g., MMRi6, MMRi61, MMRi62, MMRi63, MMRi64, MMRi65, or a combination thereof) and a pharmaceutically acceptable carrier. In another example, a composition comprises: i) one or more quinolinol compound (e.g., MMRi6, MMRi61, MMRi62, MMRi63, MMRi64, MMRi65, or a combination thereof), and ii) Nutlin3a.

A "therapeutically effective" amount of a compound of the disclosure refers to an amount of an agent which is effective, upon single or multiple dose administration to an individual for alleviating the symptoms of, or treating a disease (e.g., cell proliferation disorder) or in prolonging the survivability of the patient with such diseases beyond that expected in the absence of such treatment. For example, "therapeutically effective" amount of a compound of the disclosure can cause apoptosis of cells in an individual (e.g., inhibit the growth of cancer cells including, but not limited to, inhibiting the growth of tumors). The exact amount desired or required will vary depending on the particular compound or composition used, its mode of administration and the like. Appropriate effective amount can be determined by one of ordinary skill in the art informed by the instant disclosure using only routine experimentation.

Accordingly, the present disclosure further provides pharmaceutical formulations comprising the compound or compounds, or a pharmaceutically acceptable salt, prodrug, or hydrate thereof, together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

Examples of pharmaceutically-acceptable carrier include pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body.

The compositions can be provided in combination with any suitable delivery form or vehicle, examples of which include, for example, liquids, caplets, capsules, tablets, inhalants or aerosol, etc. The compositions may be in a form that enhance delivery of the pharmaceuticals, such as, for example, nanoparticle, microsphere or liposome formulations, a variety of which are known in the art and are commercially available. Pharmaceutical carrier can be diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, olive oil, gel (e.g., hydrogel), and the like. Saline is a common carrier when the pharmaceutical composition is administered intravenously. Saline solutions and aqueous dextrose and glycerol solutions can also be employed as liquid carriers, particularly for injectable solutions. Examples of pharmaceutically acceptable carriers can be found in: *Remington: The Science and Practice of Pharmacy* (2005) 21st Edition, Philadelphia, Pa. Lippincott Williams & Wilkins.

In an example, a composition comprises one or more quinolinol, β-cyclodextrin, and an aqueous buffer. The composition may further comprise DMSO.

Various methods known to those skilled in the art can be used to introduce (i.e., administer) the compositions of the disclosure to an individual. For example, the present compositions can be administered in any manner including, but not limited to, orally, parenterally, sublingually, transdermally, rectally, transmucosally, topically, via inhalation, via buccal administration, or combinations thereof. Parenteral administration includes, but is not limited to, intravenous, intraarterial, intracranial, intradermal, subcutaneous, intraperitoneal, subcutaneous, intramuscular, intrathecal, and intraarticular. The compound(s) also can be administered in the form of an implant, which allows a slow release of the compound(s), as well as a slow controlled i.v. infusion.

In an aspect, the present disclosure provides methods for causing apoptosis of cells by contacting the cells with a composition comprising one or more quinolinol compound (e.g., one or more members of the MMRi6 family of compounds), and optionally further comprising one or more inhibitors of cell growth arrest. For example, the cells may be contacted with MMRi6, MMRi61, MMRi62, MMRi63, MMRi64, MMRi65, or a combination thereof, and may also be contacted with Nutlin3a. The cells may be contacted in vitro or in vivo. The cells may be contacted with a quinolinol compound (e.g., MMRi6 family) and Nutlin3a simultaneously or sequentially. A measure of effectiveness of the quinolinol compound(s) (e.g., MMRi6, MMRi61, MMRi62, MMRi63, MMRi64, MMRi65, or a combination thereof) is determination of Mdm2-Mdmx E3 ligase activity. The methods can inhibit the growth of cancer cells including, but not limited to, inhibiting the growth of tumors.

The methods can induce apoptosis in cancer cells (e.g., leukemia and lymphoma cells). The quinolinol compound(s) or composition comprising the quinolinol compound(s) can be administered to an individual (e.g., a human or non-human animal) such as, for example, an individual that has cancer (e.g., leukemia or lymphoma).

For example, a method of inducing apoptosis of cells, comprises contacting the cells with a therapeutically effective amount of one or more quinolinol compound (e.g., MMRi6, MMRi61, MMRi62, MMRi63, MMRi64, MMRi65, or a combination thereof). The method can further comprise the step of contacting the cells with Nutlin3a. For example, the cells are contacted with one or more quinolinol compound (e.g., MMRi6, MMRi61, MMRi62, MMRi63, MMRi64, MMRi65, or a combination thereof), and Nutlin3a concomitantly or sequentially.

For example, a method of inducing apoptosis of cells is carried out where the cells express wild-type or mutant p53. For example, a method for inducing apoptosis modifies and/or partially inhibits, but does not completely inhibit, the Mdm2-Mdmx ring domain.

The steps of the method described in the various embodiments and examples disclosed herein are sufficient to carry out the methods of the present disclosure. Thus, in an example, a method consists essentially of a combination of steps of the methods disclosed herein. In another example, a method consists of such steps.

In the following Statements, various examples of the methods of the present disclosure are described:

Statement 1. A method of inducing apoptosis of cells (e.g., cancer cells, such as, for example, types of cancer cells described herein) comprising contacting the cells with a therapeutically effective amount of one or more quinolinol compound of the present disclosure (e.g., a quinolinol compound having the following structure:

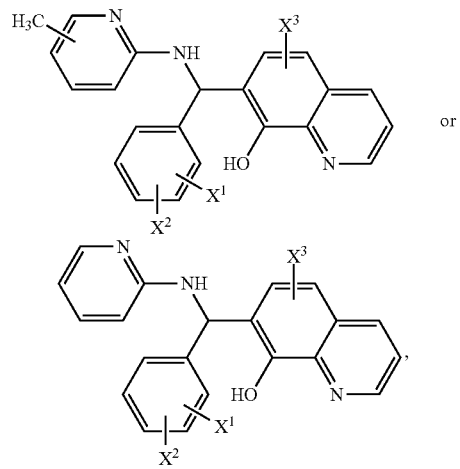

wherein the $X^1$, $X^2$, and $X^3$ substituents are independently selected from —H, —Cl, —Br, and —I).

Statement 2. A method of inducing apoptosis of cells (e.g., cancer cells) according to Statement 1, where $X^1$, $X^2$ are both —Cl.

Statement 3. A method of inducing apoptosis of cells (e.g., cancer cells) according to any one of Statements 1 or 2, where $X^1$ and $X^2$ are both —Cl and are at the 1 and 2 positions of the ring.

Statement 4. A method of inducing apoptosis of cells (e.g., cancer cells) according to any one of Statements 1 or 2, where $X^1$ and $X^2$ are both —Cl and are at the 2 and 3 positions of the ring.

Statement 5. A method of inducing apoptosis of cells (e.g., cancer cells) of according to any of Statements 1 or 2, where the quinolinol compound is selected from MMRi6, MMRi61, MMRi62, MMRi63, MMRi64, MMRi65, and combinations thereof.

Statement 6. A method of inducing apoptosis of cells (e.g., cancer cells) according to any one of the preceding Statements, further comprising contacting the cells with Nutlin3a.

Statement 7. A method of inducing apoptosis of cells (e.g., cancer cells) according to any one of the preceding Statements, wherein the cells are contacted with one or more quinolinol and Nutlin3a concomitantly or sequentially.

Statement 8. A composition comprising one or more quinolinol compound of the present disclosure having the following structure:

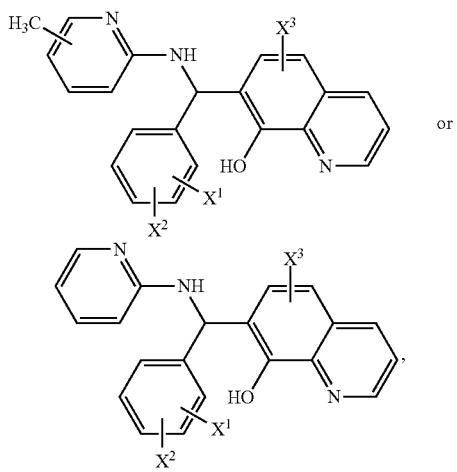

or wherein the $X^1$, $X^2$, and $X^3$ substituents are independently selected from —H, —Cl, —Br, and —I, and a pharmaceutically acceptable carrier (e.g., β-cyclodextrin).

Statement 9. A composition according to Statement 8, where the quinolinol compound is selected from MMRi6, MMRi61, MMRi62, MMRi63, MMRi64, MMRi65, MMRi68, and combinations thereof.

Statement 10. A composition according to any one of Statements 8 or 9, where the composition further comprises Nutlin3a.

The following examples are presented to illustrate the present disclosure. They are not intended to limiting in any matter.

Example 1

The following example describes examples of quinolinol compounds of the present disclosure, identification of same, and uses of same in methods of the present disclosure.

Figure 1:
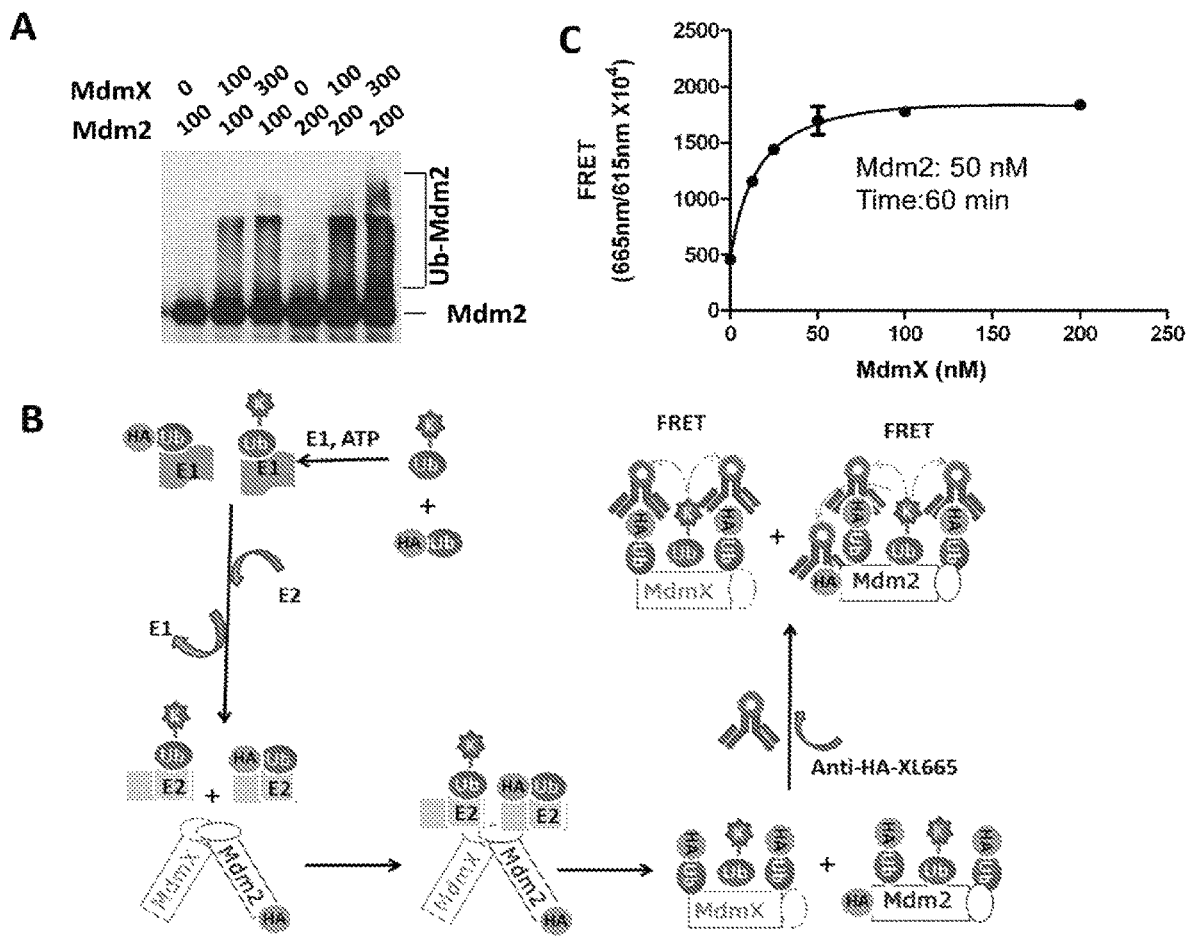
FIG. 1 shows HTS of small molecule inhibitors of Mdm2-MdmX E3 ligase activity. (A) Concentration dependent effect of Mdm2 and MdmX on Mdm2 ubiquitination. In vitro ubiquitination reaction performed with indicated concentrations (nM) of Mdm2 and MdmX recombinant proteins followed by Western Blotting (WB) for Mdm2. Ubiquitinated Mdm2 (Ub-Mdm2) and Mdm2 bands were shown. (B) Schematic illustration of FRET-based assay of Mdm2 and MdmX ubiquitination. Two fluorophores that generate FRET were conjugated to ubiquitin (Ub-K, ubiquitin-cryptate) and anti-HA antibody (Anti-HA-XL665. These two fluorophores will be brought in proximity for FRET to occur once ubiquitin chains are assembled on HA-Mdm2 and MdmX proteins. (C) MdmX concentration-dependent stimulation of FRET signals under fixed concentration of Mdm2 and reaction time. (D) Reaction time-dependent increase of FRET signals at fixed concentrations of Mdm2 and MdmX proteins. (E) Z score obtained in a test with approximately 500 compounds. (F) Summary of positive hits at different cut-offs of inhibition of FRET signals by compounds after completion of HTS of Chembridge DIVERSet™ library.
Figure 1:
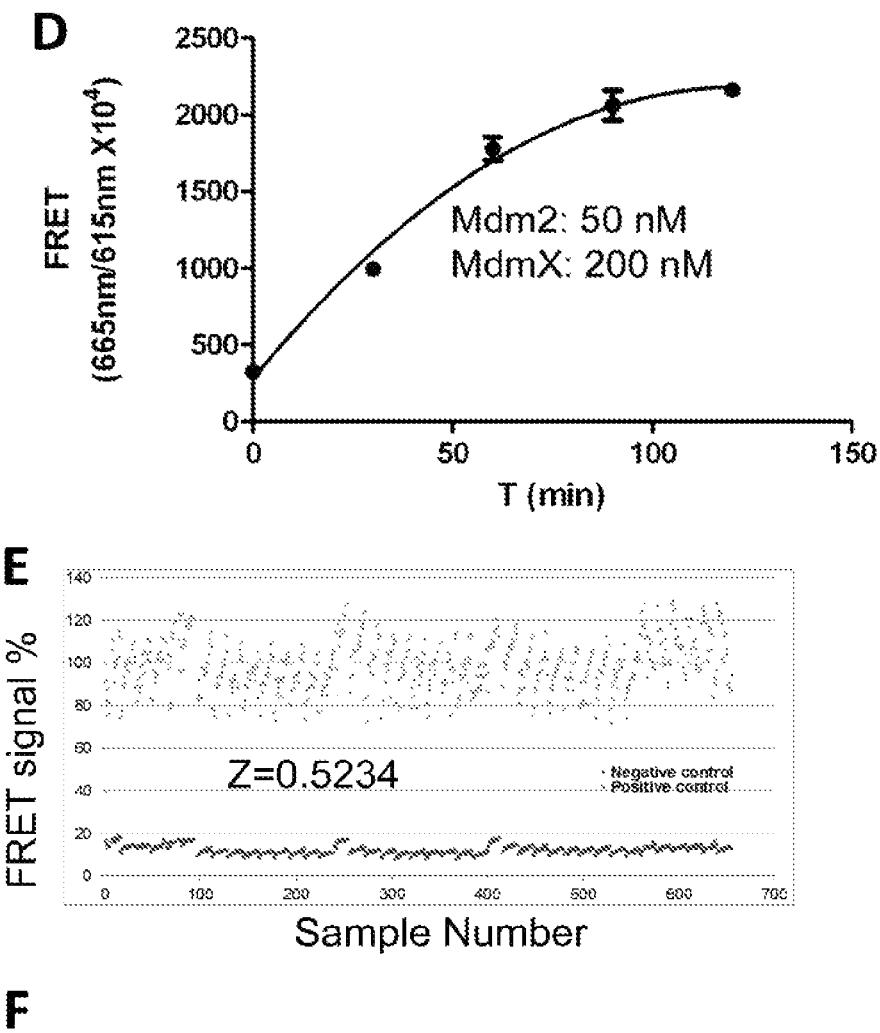

High throughput screening of small molecule inhibitors for the E3 ligase activity of Mdm2-MdmX E3 complex. It was previously reported that Mdm2-MdmX RING-RING interaction is required for p53 polyubiquitination. This RING-RING interaction also stimulates Mdm2 autoubiquitination and MdmX ubiquitination (FIG. 1A). To establish a biochemical assay for screening small molecule inhibitors of Mdm2-MdmX RING-RING interaction, we took advantage of an in vitro assay for MdmX-stimulated Mdm2 autoubiquitination as a readout of the interaction effect. To facilitate its application in HTS, we adapted our in vitro ubiquitination assay to a fluorescence resonance energy transfer (FRET) based quantification system described previously. This system uses so-called homogeneous time-resolved fluorescence (HTRF™) to quantify ubiquitin chain reactions. In this system, the fluorescence signals are generated by FRET from two fluorophore-labeled components in proximity, one is ubiquitin and another is ubiquitinated substrates. In our case, as illustrated in FIG. 1B, FRET signals were generated between anti-HA-XL665 that binds to HA-Mdm2 and HA-ubiquitin and ubiquitin-cryptate. The total FRET signal from our reaction collectively reflects ubiquitin chains formed on Mdm2 and MdmX. Our optimized reaction produces ~8-fold FRET fluorescence signals in an MdmX concentration-dependent manner (FIG. 1C) and reaction-time-dependent manner (FIG. 1D). After adaption of this assay in HT format, we performed an initial screen of ~650 samples. The Z'-factor of this HTS assay was determined to be 0.52 (FIG. 1E), indicating a suitable and reliable HTS screen assay (FIG. 1E). Then we used this HTS assay and completed screening of a diversity library (DIVERSet™, ChemBridge). Out of 55,230 compounds, we identified a number of positive hits at different inhibition cutoffs as summarized in FIG. 1F.

We showed that MdmX stimulates Mdm2 autoubiquitination in in vitro ubquitination assays with recombinant proteins (FIG. 1A). We then developed a FRET-based fluorescent assay to quantify ubiquitin conjugation of Mdm2-MdmX complex in vitro using cisbio reagents (Anti-HA-XL665 and ubiquitin-cryptate). The FRET signal is generated between ubiquitin-cryptate and fluorophore-labeled anti-HA antibody (anti-HA-XL 665 that binds to Mdm2-HA and HA-ubiquitin when ubiquitin-cryptate and HA-ubiquitin are conjugated to HA-Mdm2-HA and MdmX proteins (FIG. 1B). When Mdm2 E3 ligase activity is stimulated by MDM4, Mdm2-HA autoubiquitination is also increased and MdmX is also ubiquitinated thus generates more ubiquituin-cryptate-Mdm2-HA adducts and HA-ubiquitin-MdmX adducts, therefore higher FRET signals. We showed that the FRET signal intensities (ratios of 665 nm/615 nm) faithfully reflect the RING-RING interaction effects on Mdm2 autoubiquitination in concentration- and time-dependent manners in test tubes. We then adapted this FRET-based biochemical assay to high throughput screening (HTS) format and achieved a Z-value of 0.522 which is an acceptable score.

We used this HTS assay and completed screening of screening of DIVERSet™ drug-like library with a HT FRET-based assay, we obtained 371 positive hits at 75% cutoff.

Identification of compounds that specifically targeting Mdm2-MdmX E3 ligase activity. To evaluate the hits identified by HTS for specific inhibition of Mdm2-MdmX E3 ligase activity, we examined their ability to inhibit Mdm2 autoubiquitination, p53 polyubiquitination by Mdm2-MdmX using our in vitro biochemical assays. We used NEDD4-1 autoubiquitination as a control for non-specific inhibitors of E3 ligase activity in replicate experiments. In these assays, the ubiquitinated products were monitored by Western blotting instead of FRET assay. After validating the available ~350 hits by these validation assays, the hits fall into three categories: 1) 301 hits that fail to inhibit any of the E3 ligase activities (HTS false positive); 2) 42 pan-inhibitors of the ubiquitination system that inhibit all three ubiquitination reactions; 3) seven specific inhibitors of Mdm2-MdmX RING-RING E3 complex that inhibit both MdmX-stimulated Mdm2 autoubiquitination and Mdm2-MdmX-mediated p53 polyubiquitination, but not NEDD4-1 autoubiquitination (designated MMRi which stands for Mdm2-MdmX RING domain inhibitors). As summarized in FIG. 2, among seven MMRis, three strongly inhibit p53 ubiquitination by Mdm2-MdmX. We used Nutlin3a as a negative control. In contrast to MMRis, Nutlin3a as an Mdm2-p53 binding inhibitor had no effect on Mdm2-MdmX-mediated p53 polyubiquitination in our assay at the same concentration (FIG. 2C, Nutlin3a), indicating that MMRis inhibit Mdm2-MdmX via distinct mechanisms of action from Nutlin3a. Of note, this study also identified a group of compounds that inhibits both Mdm2-MdmX complex and NEDD4-1 E3 ligase (designated as MMNi, stands for Mdm2-MdmX and NNEDD4-1 inhibitors) as represented by MMNi1 in FIG. 2.

Validation of the hits with alternative methods using in vitro ubiquitination assays identified 7 specific inhibitors for Mdm2-MdmX, designated as MRRi. We showed that these MMRis inhibit Mdm2 autoubiquitination stimulated by MdmX (FIG. 2A) and also p53 ubiquitination by Mdm2-MdmX (FIG. 2C), but, they do not inhibit NEDD4-1 E3 ligase activity.

Characterization of MMRi6 and its analogs as disruptors of Mdm2-MdmX RING-RING interaction. In an initial test of MMRis in cell culture for p53 stabilization, MMRi6 was found to be the most potent inducer of p53 stabilization (data not shown). MMRi6 is a quinolinol derivative and represented a promising class of compound for follow-up studies. Therefore, we obtained thirteen more analogs of MMRi6 commercially available for further evaluation (structures of MMRi6 and MMRi64 are shown FIG. 3D). We confirmed that MMRi6 and another five analogs MMRi61~MMRi65 can effectively inhibit MdmX-stimulated Mdm2 autoubiquitination in vitro at a concentration of 10 µM (FIG. 3A). To ask whether MMRi6 and analogs also inhibit autoubiquitination of Mdm2 RING domain, we performed experiments with Mdm2 RING domain recombinant proteins. Our results indicated that MMRi6 and MMRi61~MMRi65 do not inhibit autoubiquitination of Mdm2 RING domain at the equimolar concentration. These results suggest that MMRi6 and analogs selectively affect Mdm2-MdmX RING-RING interaction but not Mdm2-Mdm2 RING-RING interaction. To directly evaluate the ability of these compounds in inhibiting Mdm2-MdmX interaction, we performed in vitro pulldown experiments using recombinant FLAG-MdmX and HA-Mdm2RING proteins. After incubation of the two proteins in test tubes in the presence or absence of test compounds for 30 min at RT, FLAG-MdmX was pulled down with anti-FLAG beads followed by detection of MdmX-bound HA-Mdm2RING domain by Western blotting for HA-tag. Our results indicated that MMRi6 and MMRi64 effectively inhibit Mdm2-MdmX RING-RING interaction in vitro. In contrast, MMRi31, an analog of MMRi3 that strongly inhibits p53 ubiquitination by Mdm2-MdmX, has no inhibitory effect on Mdm2-MdmX interaction but slightly increased the interaction (FIG. 3C). We then performed docking analysis of MMRi62 and MMRi64 with Mdm2-MdmX RING domains using the DOCK6 program and the 3-D structure of Mdm2-MdmX RING domains. The docking results indicated that MMRi62 and MMRi64 bind to the MdmX RING domain (FIG. 3E Connolly surface). Their binding to the MdmX cleft interferes with MdmX RING domain interaction with Mdm2 RING domain (FIG. 3E ribbon diagram). Collectively, these results confirmed that MMRi6 and MMRi64 are disrupting inhibitors of Mdm2-MdmX RING domain interaction.

We chose to further characterize MMRi6 with commercially available analogs of this compound. We showed that MMRi6, MMRi61, MMRi62, MMRi63, MMRi64, MMRi65 inhibit Mdm2 autoubiquitination stimulated by MdmX (FIG. 23A). However, they do not inhibit Mdm2 ubiquitination by RING-RING homo-dimers using Mdm2-B isoform (FIG. 3B). Using recombinant proteins FLAG-MdmX and HA-Mdm2 in an in vitro pulldown assay, we show that Mdm2-MdmX interaction is inhibited by MMRi6 and MMRi64 (FIG. 3C). By molecular docking analysis, we show that MMRi62 and MMRi64 bind to a cleft of MdmX RING domain that interfere with its binding to Mdm2 RING domain (FIG. 3D).

Activation of the p53 pathway by MMRi. Using HCT8, a wild type p53-bearing colon cancer cell line, we tested the activity of our MMRis in activating the p53 pathway. In this cell system, MMi6 and its analogs appear to be the most potent inducer of p53 protein stabilization (FIG. 4A). Therefore, MMRi64 was further followed up for more cellular experiments of characterization. In HCT8 cells, MMRi64 at 5 µM induced a time-dependent p53 accumulation accompanied with induction of its target gene product Mdm2 (FIG. 4B, left panel). MMRi64 also induced a concentration-dependent induction of p53 accumulation which is evident at as low as 0.31 µM in HCT8 cells (FIG. 4B, right panel). Interestingly, MMRi64 induces significant downregulation of MdmX in a time-dependent and concentration-dependent manner (FIG. 4B), which is not obvious with Mdm2-p53 inhibitor Nutlin3a (FIG. 4B, right panel). To test whether MMRi64 also activate p53 in other cancer types, we performed experiments with pre-B acute lymphoblastic leukemia NALM6 cells that bear wild type p53. As indicated in FIG. 4C, MMRi64 was capable of activating p53 in NALM6 cells as well in a time-and-concentration dependent manner. Surprisingly, in contrast to HCT8 cells in which Mdm2 was upregulated upon p53 activation by MMRi64, in NALM6 cells Mdm2 expression was strongly reduced by MMRi64, in addition to MdmX downregulation. To determine whether Nutlin3a has the similar effect on Mdm2 and MdmX in NALM6 cells, we performed a similar experiment with Nutlin3a. As shown in FIG. 4C left panel, Nutlin3a induced a strong induction of Mdm2 protein and slightly decreased MdmX levels. These data indicated that MMRi64 has unique inhibitory effect on Mdm2 and MdmX expression levels in leukemic cells.

MMRi64 potently induces p53-dependent and p53-independent apoptosis in lymphoma cells. The strong effect of MMRi64 on Mdm2 and MdmX downregulation prompted us to further test the antitumor effect of MMRi64 in lymphoma cells. We focused on apoptosis induction by this compound because p53-dependent apoptosis is a critical mechanism for preventing lymphomagenesis and the outcome of lymphoma treatment. In NAML6 cells, MMRi64 at 1 µM induced a time-dependent induction of PUMA, a critical pro-apoptotic downstream gene product of p53. Interestingly, p21, the growth-arresting effector target gene of p53 was transiently induced then downregulated to a level lower than basal p21 expression at 24 h of the treatment. Accompanied with the activation of p53's pro-apoptotic arm of the p53 response, cleavage of PARP by activated caspase 3 is evident at 8 h and further increased at 24 h after treatment. These data indicated that MMRi64 triggered activation of the intrinsic apoptosis pathway. To ask whether Nutlin3a as an Mdm2-p53 targeting compound has the similar capacity to induce apoptosis in NALM6 cells, we used Nutlin3a in a similar experiment. Our results showed that Nutlin3a, at the same concentration of 1 µM as used in MMRi64 experiment, induced stronger p53 accumulation and PUMA induction than MMRi64 (FIG. 5A, middle panel). However, in contrast to MMRi64 treatment, Nutlin3a also induced strong induction of growth-arresting effector p21 (FIG. 5A, right panel). Accompanied with these molecular events, cleavage of PARP and activation of caspase 3 were barely detectable in Nutlin3a treated cells for 24 h, even though Nutlin3a induced a similar level of p53 accumulation at this time point (FIG. 5A right panel). Together, these results indicated that activation of the p53 pathway by Nutlin3a mainly results in cell growth arrest while p53 activation by MMRi64 mainly causes apoptosis in NALM6 cells. To determine whether MMRi64-induced apoptosis in lymphoma cells is p53-dependent, we performed experiments with Emu-myc mouse lymphoma cells of different p53 status. As expected, MMRi6 induced a p53 accumulation in wt-p53 cells at as low as 0.1 µM (FIG. 5B, upper panel). PARP cleavage can be detected at 24 h by ~0.5 µM MMRi6 treatment in wt-p53 Emu-myc lymphoma cells but not in p53-null Emu-myc lymphoma cells (FIG. 5B, lower panel). Therefore, the MMRi6-induced apoptosis in lymphoma cells contains a p53-dependent component. The ability of MMRi64 to induce apoptosis was further analyzed by flow cytometry. Our results show that MMRi64 at 0.5 µM and 1 µM for 48 h induced 7.3% and 20% sub-G1 population, respectively. In contrast, Nutlin3a at 0.5 µM, 1 µM and 2 µM for 48 h only induced 0.4%, 0.8%, and 3.0% subG1 populations, respectively (FIG. 5C). Together, these results indicate that MMRi64 preferentially induces apoptosis in NALM6 cells.

To further confirm the p53-dependence of MMRi64-induced growth inhibition, we used mouse Emu-myc lymphoma cells of wt-p53 and p53-null background in growth inhibition experiments. In an 72 h cell proliferation assay in the presence or absence of MMRi6, we found that the $IC_{50}$ of MMRi6 was ~0.5 µM and ~3 µM for wt-p53 and p53-null Emu-myc lymphoma cells, respectively, indicating that p53 contributes a ~6-fold difference in MMRi6 sensitivity in this set of mouse lymphoma cells (FIG. 6A, data from two doses were shown). Then we used HCT116 and HCT116-p53-/- cells to further test the contribution of p53 to MMRi64-induced anti-growth effect. As shown in FIG. 6B, at equimolar concentrations of Nutlin3a, p53 contributes to a maximal ~35% more growth inhibition than in HCT116-p53--/- cells, whereas p53 contributes to a maximal ~10% more growth inhibition in MMRi64 treatment. Therefore, MMRi64 inhibits cell growth through p53-dependent and p53-independent mechanisms.

MMRi64 and Nutlin3a activate p53 through distinct mechanisms of action. To understand whether low concentrations of MMRi64 and Nutlin3a will synergistically inhibit cell growth by apoptosis, we performed combination experiments with the two compounds in NALM6 cells. First, we looked at apoptotic PARP cleavage during single and combination treatment. Our results show that 1 µM Nutlin3a and 1 µM MMRi64 induced similar levels of p53 accumulation at 8 h and 24 h. However, only MMRi64 induced obvious PARP cleavage at 8 h and 24 h. Yet, combination of the two compounds dramatically induced p53 and PARP cleavage at two time points. Then, we used flow cytometry to measure apoptotic sub-G1 population after drug treatment. Single treatment at low concentrations with either Nutlin3a or MMRi64 induced small increase in sub-G1 populations (0.73%, and 2.5% for 0.2 µM or 0.4 µM of MMRi64, respectively, and 1.3% for 2 µM Nutlin3a). As expected, the combination of Nutlin3a-MMRi64 at two concentrations induced significant increase in subG1 populations: 8.7% for 2 µM Nutlin3a-0.2 µM MMRi64 combination and 16% for 2 µM Nutlin3a-0.4 µM MMRi64 combination. Taken together, these results indicated that combinations of MMRi64 and Nutlin3a synergistically kill lymphoma cells by apoptosis.

Discussion Targeting Mdm2-p53 interaction for p53 restoration in cancer therapy has been pursued for many years. These efforts led to identification of several promising compounds with remarkable therapeutic activity in preclinical systems. Recent advancement of several compounds to early clinical trials with hematological malignancies and certain types of solid tumor ignited renewed enthusiasm for p53-based cancer therapy. Nutlin3a was the first and potent specific inhibitor of Mdm2-p53 interaction and served as a prototype for chemical optimization and fostered discovery of compounds with better drug properties and efficacy. However, one potential and prominent concern is that MdmX overexpression confers resistance to Nutlin3a treatment in various cell types. This problem is likely to hinder the use of other Mdm2-p53 targeting compounds. Together with the radioresistant lymphoma phenotype of non-degradable MdmX mutant mice, these findings point to MdmX as another valid drug target for p53-based cancer therapy. Using an elegant mouse model, it was previously demonstrated that MdmX is a better drug target than Mdm2 in lymphoma. To overcome MdmX-mediated resistance, efforts have been made to identify peptide inhibitors or small molecule inhibitors that target both Mdm2-p53 and MdmX-p53 interfaces. Served as a proof of principle, results from a dual inhibitor peptides and compounds demonstrated better p53-dependent cytotoxic effect in breast and colon cancer cells.

Differing from the focus of the field, we turned our interest in Mdm2-MdmX RING-RING interaction based on our biochemical findings from our lab and genetic evidence from other's studies. This report is the first attempt to identify a new class of p53-activating agent and assess the effectiveness of targeting this newly established interface. To our surprise, MMRi64 not only disrupts Mdm2-MdmX interaction in vitro, but also induces significant MdmX downregulation in cancer cells. Once p53 is activated, Mdm2 will be induced by a feedback regulatory loop. Although p53-dependent Mdm2 induction was observed in HCT8 cells (FIG. 4B), Mdm2 was not induced in lymphoma cells (FIG. 4C). The mechanisms underlying this cell-type difference in Mdm2 induction are not known at present. We speculate that this may be due to the differential effect of MdmX on Mdm2 protein stability, i.e., MdmX plays a crucial role to stabilize Mdm2 proteins in lymphoma cells but not a crucial role in colon cancer cells. This hypothesis needs further experimentation to test. This cell type-specific effect of MMRi64 on Mdm2 and MdmX makes it a desirably compound for lymphoma treatment.

We tested MMRi64 mainly in leukemia/lymphoma cells because the p53 pathway is critical for apoptosis induction and restoration of p53 in mice leads to regression of autochthonous lymphomas. The importance of the p53 pathway was also demonstrated in the Emu-myc lymphoma models. Intriguingly, in human lymphoma, p53 mutation is relatively low and about 80-90% lymphoma patients have a wt-p53 status. In Diffuse Large B-cell Lymphoma p53 mutation rate is as low as 4.2% (TCGA data). Therefore, p53 restoration therapy would benefit a large group of lymphoma patients. The therapeutic outcome of p53-based therapies relies on drug-induced apoptosis since p53-dependent anti-lymphoma effect is mainly mediated by apoptosis. In sharp contrast to Nutlin3a, our lead MMRi64 preferentially induces apoptosis in leukemia/lymphoma cells. This is accompanied with time-dependent induction of pro-apoptotic PUMA and simultaneous shutdown of pro-growth-arrest p21 (FIGS. 4 & 5A) and downregulation of Mdm2 and MdmX. Whether the selective effect of p53 downstream gene induction by MMRi64 is due to its effect on MdmX or Mdm2 needs to be tested by future experiments.

The mechanisms for why MMRi64 preferentially induces apoptosis compared to Nutlin3a is presently unknown. However, we speculate that downregualtion of Mdm2 and/or MdmX by MMRi64 might be an explanation. Several lines of evidence support this notion. Downregulation of Mdm2 by MI-219 appears to be associated with p53-dependent apoptosis in follicular lymphoma. It was previously reported that using animal models demonstrated that p53 restoration in Mdm2-overexpressing tumors inhibits proliferation but not inducing apoptosis, suggesting high levels of Mdm2 has anti-death activity. Moreover, siRNA knockdown experiments revealed that Mdm2 is actually required for p53-dependent induction of p21 to cause growth arrest. All these findings are consistent with the reduced levels of Mdm2 and weak induction of p21 by MMRi64 treatment. Shutdown of p21 induction by p53 in the absence of Mdm2 in MMRi64-treated cells favors apoptosis induction in MMRi64-treated cells since p21 serves as an inhibitory effector for p53-dependent apoptosis as demonstrated in colon cancer cells. Beyond a role of Mdm2 in p53-dependent apoptosis, Mdm2 was reported to promote p53-independent lymphomagenesis and confer p53-independent drug response. This role of Mdm2 was revealed by Mdm2 splice isoforms that do not have p53-binding domain but can promote Emu-myc lymphomagenesis in a manner comparable with full-length Mdm2. Loss of Mdm2 expression in MMRi64-treated cells is probably due to MdmX downregulation by MMRi64, since MdmX is required for p53 binding to Mdm2 promoter and full induction of Mdm2 in stressed cells 51 and MdmX can stabilize Mdm2 protein by inhibiting its autoubiquitination.

MMRi64 belongs to a chemical class of quinolinol family in which inhibitors of botulinum neurotoxins and two anti-cancer derivatives were recently reported. The inhibitor of botulinum neurotoxin has shown excellent toxicity profile which favors exploration of this chemical class in cancer drug discovery. Owing to the unique effects of MMRi64 on the critical components of the p53 regulatory loop and downstream effectors, MMRi64 may be used as a pharmaceutical tool to dissect the molecular regulation of p53-dependent transactivation program. Therefore, this study identified a new class of chemicals that might be useful in basic research on p53-dependent biology as well as development of new p53/Mdm2/MdmX-based cancer therapeutics.

Materials and Methods. Plasmids, Protein Purification, and Chemical Reagents. FLAG-MdmX and HA-Mdm2 (human) constructs for insect cell expression and protein purification were described previously. HA-ubiquitin construct was generated by inserting HA-tag to the N-terminus of ubiquitin in pET28a vector. The mammalian expression plasmid pcDNA3.1-HdmX was a gift from Dr. Gokul Das (Roswell Park Cancer Institute). HA-Mdm2RING domain was generated by site-directed mutagenesis to loop out aa28-299 using pFAST-bac-HA-Mdm2 as a template and the recombinant baculovirus was prepared and protein was expressed in insect cells as described previously.

HCT-8 was used in our recent studies and originally purchased from ATCC and were maintained in Dulbecco's Modified Eagle's Medium (DMEM) supplemented with 10% fetal calf serum (FCS, Atlanta Biologicals, Inc. GA, USA) and antibiotics. HCT116 and HCT116-p53−/− cells were originally provided to Dr. Terry Beerman by Prof. B. Vogelstein (Johns Hopkins University, Baltimore, Md.). These cells were received in 2004 and cultured in McCoy's 5A containing 10% fetal bovine serum in an atmosphere of 5% CO2. Pre-B Acute lymphoblastic leukemia cell line NALM6 cells were obtained from Fengzhi Li (RPCI) and cultured in RPMI-1640 supplemented with 10% fetal calf serum (FCS, Atlanta Biologicals, Inc. GA, USA) and antibiotics. Emu-myc lymphoma cells of wt-p53 and p53-null background were kind gifts from Dr. Scott Lowe and Dr. Clare Scott, respectively. These cells were cultured in the high-glucose version of Dulbecco modified Eagle medium supplemented with 10% fetal calf serum, penicillin/streptomycin, 0.1 mM L-asparagine and 50 µM 2-mercaptoethanol.

Compounds were purchased from Hit2lead Chembridge Online Chemical Store (San Diego, Calif. 92121). All the compounds were dissolved in DSMO as 20 mM stock. Nutlin3a was purchased from Cayman Chemical Company (Ann Arbor, Mich.). Antibodies for p53 (DO-1 and 1801) and p21 (H-164) were purchased from Santa Cruz. Rabbit antibodies against PUMA (D30C10), Bcl-2 (50E3), PARP (46011D) and cleaved caspase 3 (D175) were purchased from Cell Signaling Technology (Danvers, Mass.). Monoclonal antibodies for Mdm2 (2A9 and 4B11) were kind gifts from Dr. Moshe Oren (Weizmann Institute of Science, Rehovot, Israel). The Rabbit polyclonal antibody for MdmX was purchased from Proteintech (Cat #17914-1-AP). Anti-FLAG was from Sigma (M2, F1804)) and Anti-HA (HA.11) was from Covance (Princeton, N.J.). Anti-HA-XL665 (610HAXLB) and ubiquitin-cryptate (61UBIKLB) were purchased from Cisbio (Bedford, Mass.) and reconstituted according to manufacturer's instruction.

FRET-based in vitro ubiquitination assay. FRET-based in vitro ubiquitination assay was adapted from the protocol of HTRF™ described previously. HTRF™ is a homogeneous method which combines standard FRET technology with time-resolved measurement of fluorescence. The HTRF emission were measured at two different wavelengths, 615 nm (donor) and 665 nm (acceptor). In the MdmX stimulated Mdm2 auto-ubiquitination reaction, the ubiquitin cryptate and HA-tagged ubiquitin were incorporated into the ubiquitin chain. FRET is generated when the XL665 labeled anti-HA antibody binds to the HA-tagged Hdm2 or HA-tagged ubiquitin. The amounts of each reagent and recombinant protein were optimized before being adapted to high through format with concoction for two premixtures for convenient handling by a robot hand.

High throughput screening with the method of HTRF™. The pre-reaction mixture one consisted of 40 mM Tris-HCl (pH 7.5), 5 mM MgCl2, 2 mM DTT, 5 mM ATP, 20 nM E1, 350 nM E2 (UbcH5), 25 nM HA-tagged Mdm2, 200 nM MdmX. Firstly, 10 µL of the pre-reaction one was dispensed in each well of 384 well plate (Multiflo™, Biotek). Then compounds from a chemical library (DIVERSet™, ChemBridge) were added in a volume of 8 nL of each by the robot pin tool (PerkinElmer JANUS, V&P Scientific 384 Pin tool). The reaction was started by adding premixture two which consisted of 250 nM HA-tagged ubiquitin and 50 nM ubiquitin-cryptate at 2 µL per well. After incubation at 37° C. for 1.5 h, the reaction was terminated by adding 10 µL of the detection buffer, which contains 50 mM phosphate buffer pH 7.0, 0.1% BSA, 0.1 M EDTA, 0.8 M KF and 20 nM XL665-conjugated antibody against HA tag. The reaction was kept for 1 hour at room temperature prior to measuring the FRET signal. For the FRET measurement in Perkin Elmer Envision 2103 Multilabel Reader, there is a 100 µs time delay between the excitation (320 nm) and measurement at two different wavelengths (615 nm and 66 5 nm), then calculating the ratio for each well individually. (Ratio=665 nm/615 nm×10⁴). The 10⁴ multiplying factor is introduced for convenient data processing.

In vitro validation assays by Mdm2 autoubiquitination and p53 ubiquitination by Mdm2-MdmX and NEDD4-1 autoubiquitination. In order to test the compound specificity, we used two sets of ubiquitination reaction. One is MdmX stimulated Mdm2 autoubiquitination, the other is NEDD4-1 autoubiquitination. The two reactions share the same constitutes in the premixture: 40 mM Tris-HCl (pH 7.5), 5 mM MgCl2, 2 mM DTT, 5 mM ATP, 20 nM E1 and 350 nM E2 UbcH5c and 10 µM of ubiquitin. The former reaction includes 100 nM HA-tagged Mdm2 and 200 nM MdmX, and latter reaction includes 200 nM HA-tagged NEDD4-1. After adding compound to final concentration of 10 µM, the reaction was started by incubation at 30° C. in a water bath for one hour. Then the reaction was stopped by adding SDS sample buffer, followed by SDS-PAGE and Western blot analysis for HA or NEDD4-1. In vitro assays for p53 ubiquitination by Mdm2-MdmX were performed as described previously. Briefly, reactions were carried out as described above for Mdm2 autoubiquitination except for addition of 100 nM p53. Compounds or DMSO of final concentrations of 10 µM were added in the reaction before starting the reaction at 30° C. for 1 h followed by WB of p53 with DO-1 antibody.

Proliferation and apoptosis assays. Growth inhibition assays and apoptosis assays were carried out as described previously.

RING domain interaction between Mdm2 and MdmX by in vitro pulldown assay. HA-tagged Mdm2RING domain (500 nM), Flag-tagged MdmX (250 nM) and testing compound (10 µM) were mixed together in 50 µL NP40 buffer (0.5% NP40, 150 mM NaCl, 20 mM Tris-HCl, pH 8.0). After 30 min incubation, the protein mixture was diluted with 450 µL NP40 buffer-0.5% BSA. 10 µL of anti-FLAG antibody conjugated M2 beads (Sigma: A2220) preincubated with NP40 buffer containing 0.5% BSA for 30 min at RT were added into the mixture to pulldown the Flag-MdmX by rotating at RT for 2 h. After 5 times washing by the NP40 buffer-0.5% BSA, the M2 beads were eluted with 45 µL 0.2 mg/ml 3×Flag peptides (in 20 mM Tris-HCl, pH 7.5, 10 mM NaCl, 1 mM DTT) to release FLAG-MdmX and its interacting proteins. The FLAG-MdmX bound HA-Mdm2RING was detected by SDS-PAGE followed by western blot analysis for HA-Mdm2 by using ant-HA antibody.

Docking analysis. Docking studies were carried out in order to investigate the preferential binding mode geometry of the compounds. The steps were performed as instructed by DOCK6 software package (dock.compbio.ecsf.edu) including all default parameter set. 3-D grids were defined for the interaction with the compounds. Docking results were examined using the Chimera program (http://www.c-gl.ucsf.edu/chimera/) to observe the interaction precisely at atomic level. Chimera was also used to manipulate the Mdm2-MdmX RING structures with the utilities for deleting solvents and adding charges.

Example 2

The following example describes examples of quinolinol compounds of the present disclosure used to treat wildtype NALM6 cells, as well as mutated NALM6-shp53 cells.

TABLE 1

Cell proliferation assay was performed with NALM6 and NALM6-shp53 cells treated with indicated drugs for 72 h (h = hour(s)).

| Compounds | IC$_{50}$ of Compounds (µM) | | |
|---|---|---|---|
| | NALM6 | NALM6-shp53 | Fold change |
| Etopside (nM) | 2.23 | 19.95 | 9x |
| Nutlin3a | 1.27 | 4.28 | 3.4x |
| MMRi64 | 0.145 | 0.14 | 1.0x |

We further found that p53 is not required for MMRi64-induced apoptosis since ShRNA knockdown of p53 in NALM6 cells did not affect apoptosis induction by MMRi64, nor did it affect MMRi64 sensitivity in anti-proliferation assays (Table 1). This result suggests that MMRi64 will have an anti-tumor effect in p53 mutant tumor cells, which are difficult to treat tumors because of resistance to current therapies.

A desirable therapeutic window of tumor-selective killing is important for a new drug candidate. To find out the therapeutic window for MMRi64, we assessed MMRi64 toxicity to normal bone marrow cells in comparison with drug-resistant lymphoma cells (RL4RH and Raji4RH cells). The effect of MMRi64 on mouse bone marrow cells was measured in granulocyte and monocyte colony forming assays (CFU-GM). The IC$_{50}$ for MMRi64 in this assay was 1.6 µM in a 7-day continuous treatment (Table 2). This IC$_{50}$ was ~1.6 to 8 fold higher than the IC$_{50}$'s of RL4RH and Raji4RH cells (IC$_{50}$ BM/C in Table 3). This is a promising therapeutic window, especially considering the CFU-GM test is 7-day treatment while the RRCL proliferation assay was a 3-day treatment. In contrast, etoposide, the first line chemotherapy for lymphoma/leukemia, had an IC$_{50}$ of 0.32 µM for CFU-GM and 1.7 to 6.5 µM for RL4RH and Raji4RH cells. Thus, etoposide was 5 to 20 fold more toxic to normal mouse bone marrow cells relative to RRCLs. In other words, etoposide is 5 fold more toxic to normal mouse bone marrow cells, but MMRi64 is 5 to 10 fold more effective to inhibit RL4RH and Raji4RH cells.

For the bone marrow toxicity assay, the following method was used. 400 µL of murine marrow mononuclear cells (2.0×10⁵/mL) in IMDM containing 20% FBS, 10 units/mL recombinant murine GM-CSF, 10% of a 10× drug solution or control solution (DMSO), and 0.3% agarose were pipetted into microwells containing a 0.4-mL underlayer of IMDM and 0.3% agarose. The cultures were allowed to gel at 4° C. for 15 min and incubated at 37° C. in a fully humidified atmosphere of 5% CO$_2$ in air for 7 days. CFU-GM colonies (aggregates of ≥40 cells) were counted with an inverted microscope using phase contrast. Percent survivals were calculated as 100× (the number of colonies in the drug-treated groups divided by the number of colonies in the vehicle control-treated group). IC$_{50}$ values were determined.

TABLE 2

| | IC$_{50}$ μM Etoposide | TW BM/CC | IC$_{50}$ μM MMRi64 | TW MB/CC |
|---|---|---|---|---|
| RL4RH | 6.3 | −19x | 1 | 1.6x |
| Raji4RH | 1.7 | −5x | 0.18 | 8x |
| CFU-GM | 0.32 | | 1.6 | |

MMRi64 has a better therapeutic window than etoposide.

Although the present disclosure has been described with respect to one or more particular embodiments and/or examples, it will be understood that other embodiments and/or examples of the present disclosure may be made without departing from the scope of the present disclosure.

The invention claimed is:

1. A method of inducing apoptosis of cells comprising contacting the cells with a therapeutically effective amount of a compound having the following structure:

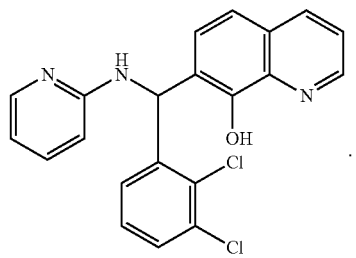 [SMILES: Oc1c(C(Nc2ccccn2)c2cccc(Cl)c2Cl)ccc2cccnc12]

2. The method of claim 1, further comprising contacting the cells with one or more inhibitor of Mdm2-Mdmx RING-RING interaction.

3. The method of claim 2, wherein the cells are contacted with

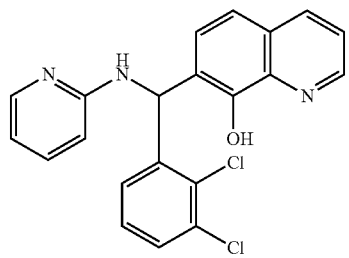

and one or more inhibitor of Mdm2-Mdmx RING-RING interaction concomitantly or sequentially.

4. A composition comprising a compound having the following structure:

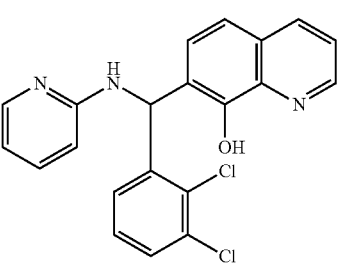 [SMILES: Oc1c(C(Nc2ccccn2)c2cccc(Cl)c2Cl)ccc2cccnc12]

and a pharmaceutically acceptable carrier.

5. The composition of claim 4, wherein the composition further comprises one or more inhibitor of Mdm2-Mdmx RING-RING interaction.

* * * * *